United States Patent
Barwick

(10) Patent No.: US 6,866,147 B2
(45) Date of Patent: Mar. 15, 2005

(54) STERILIZATION CASE FOR SURGICAL INSTRUMENTS

(75) Inventor: David Barwick, McAfee, NJ (US)

(73) Assignee: Pilling Weck Incorporated, Research Triangle Park, NC (US)

( * ) Notice: Subject to any disclaimer, the term of this patent is extended or adjusted under 35 U.S.C. 154(b) by 165 days.

(21) Appl. No.: 10/076,873

(22) Filed: Feb. 12, 2002

(65) Prior Publication Data

US 2003/0150758 A1 Aug. 14, 2003

(51) Int. Cl.[7] .............................................. B65D 83/10
(52) U.S. Cl. ....................... 206/363; 206/370; 206/45.2
(58) Field of Search ................................. 206/363, 369, 206/370, 372, 373, 45.24, 45.23, 817, 804, 742, 743, 379, 349; 422/300; 220/212, 23.86; 312/309, 311

(56) References Cited

U.S. PATENT DOCUMENTS

| | | | | |
|---|---|---|---|---|
| 2,792,935 A | * | 5/1957 | Rocchetti | 206/379 |
| 2,988,209 A | * | 6/1961 | Parrilla | 206/362 |
| 3,589,505 A | * | 6/1971 | Burniski | 206/250 |
| 4,619,364 A | | 10/1986 | Czopor, Jr. | |
| 4,773,536 A | | 9/1988 | Rau | |
| 4,934,530 A | | 6/1990 | Riess | |
| 4,955,478 A | | 9/1990 | Rau et al. | |
| 5,098,235 A | | 3/1992 | Svetlik et al. | |
| 5,193,672 A | * | 3/1993 | Long | 206/45.2 |
| 5,301,807 A | * | 4/1994 | Donahue | 206/370 |
| 5,330,056 A | * | 7/1994 | de la Rocha | 206/581 |
| 5,894,925 A | * | 4/1999 | Sukiennik et al. | 206/356 |
| 5,927,493 A | * | 7/1999 | Colombo | 206/372 |
| 5,951,385 A | | 9/1999 | Newhouse et al. | |
| 6,024,218 A | | 2/2000 | Knoblauch | |
| 6,260,701 B1 | | 7/2001 | Katayama et al. | |
| 6,283,291 B1 | | 9/2001 | Vasudeva et al. | |

* cited by examiner

Primary Examiner—Jila M. Mohandesi
(74) Attorney, Agent, or Firm—Hughes Hubbard & Reed LLP; Ronald Abramson; Peter A. Sullivan

(57) ABSTRACT

A sterilization case in which the upper portion of one side of the case functions as a door having a hinge that is positioned horizontally with respect to the height of the case. When the case is closed, the surgical instruments are held securely in position, resting against an internal tray. When the door of the case is opened, the internal tray is raised, thus making the instruments more accessible by elevating them to a position above the top of the open case. The door swings downward to form an angle with the lower portion of the case, acting as a support so that the open case can stand in an upright position. When the door is closed, the internal tray is lowered and the instruments automatically retract into the case. Holes in the front and back covers of the instrument case allow the instruments within the case to be sterilized without removing them from the case.

5 Claims, 3 Drawing Sheets

STERILIZATION CASE FOR SURGICAL INSTRUMENTS

BACKGROUND OF THE INVENTION

1. Field of the Invention

The present invention is in the field of surgical apparatus, and more particularly relates to a sterilization case for surgical instruments, for example, surgical drill bits.

2. Description of Related Art

In the current state-of-the-art, surgical instruments are frequently stored in cases. For example, surgical drill bits are conventionally stored in metal cases that lie flat and have a hinged bit-holding member that can be lifted into an upright position for access. One drawback of the conventional storage case is that the case takes up a relatively large amount of table space. Another disadvantage is that the hinged bit-holding member may not be stable in the upright position. An additional disadvantage of conventional instrument cases is that the drill bits are not necessarily easy to access during surgery.

BRIEF SUMMARY OF THE INVENTION

Accordingly, it is an object of the present invention to provide a sterilization case for surgical instruments that can be placed directly into an autoclave. It is another object of the invention to provide a sterilization case that is self-contained (i.e., that has no loose pieces which may be misplaced), even when the case is open. It is a further object of the invention to provide a sterilization case that stands in the upright position during use. It is yet another object of the invention to provide a sterilization case that offers increased accessibility of the instruments during surgery.

These and other objects of the invention are achieved with a sterilization case in which the upper portion of one side of the case functions as a door having a hinge that is positioned horizontally with respect to the height of the case. When the case is closed, the surgical instruments are held securely in position, resting against an internal tray. When the door of the case is opened, the internal tray is raised, thus making the instruments more accessible by elevating them to a position above the top of the open case. The door swings downward to form an angle with the lower portion of the case, acting as a support so that the open case can stand in an upright position. When the door is closed, the internal tray is lowered and the instruments automatically retract into the case. Holes in the front and back covers of the instrument case allow the instruments within the case to be sterilized without removing them from the case.

The details of this and other embodiments will be more apparent from a review of the accompanying drawings and of the description that follows.

DETAILED DESCRIPTION OF THE PREFERRED EMBODIMENTS

One particular embodiment of the invention is illustrated in FIGS. 1–4, and is described in the text that follows. Although the invention has been most specifically illustrated with a particular embodiment, its should be understood that the invention concerns the principles by which the claimed apparatus may be constructed, and is by no means limited to the specific embodiments shown.

Figure 1:
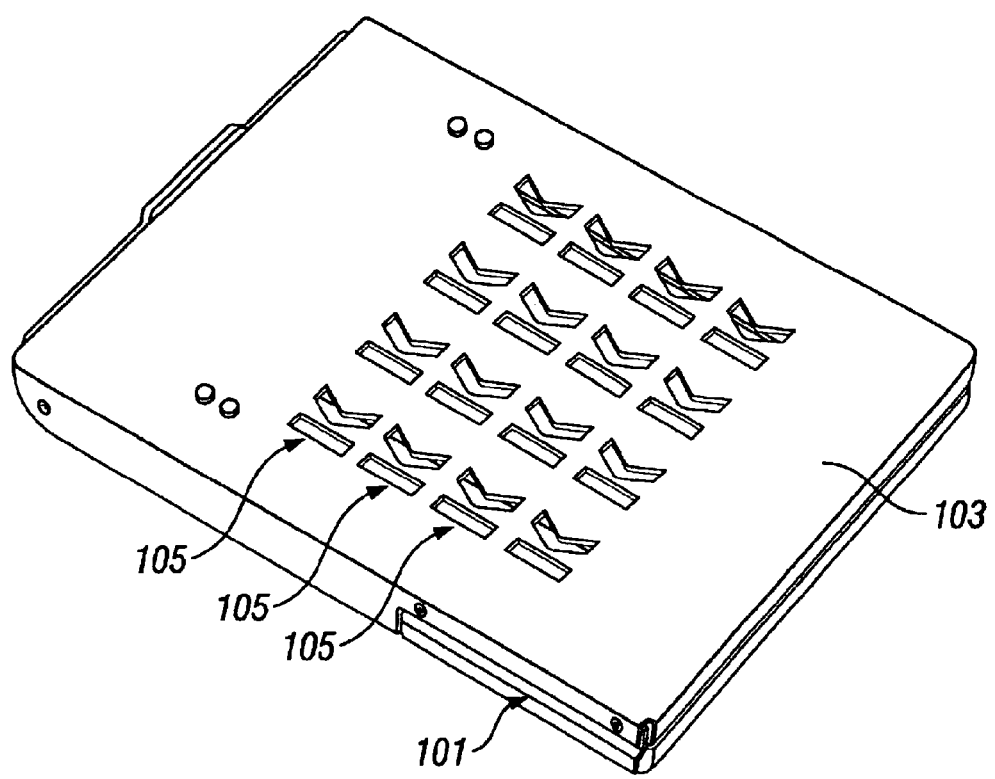
FIG. 1 is an isometric view showing the front cover of the invention.

FIG. 1 is an isometric view of one embodiment of the invention, showing front cover 103 of sterilization case 101. Holes 105 in front cover 103 allow instruments inside case 101 to be sterilized without removing them from case 101. For example, a closed case 101 with instruments inside may be placed in an autoclave, and holes 103 will permit the instruments inside case 101 to be sterilized. Holes 105 may be of any size, shape or number that allows sufficient flow of the sterilization fluid through case 101 (e.g., holes 105 as shown in FIG. 1 are in the shape of a "K."

Figure 2:
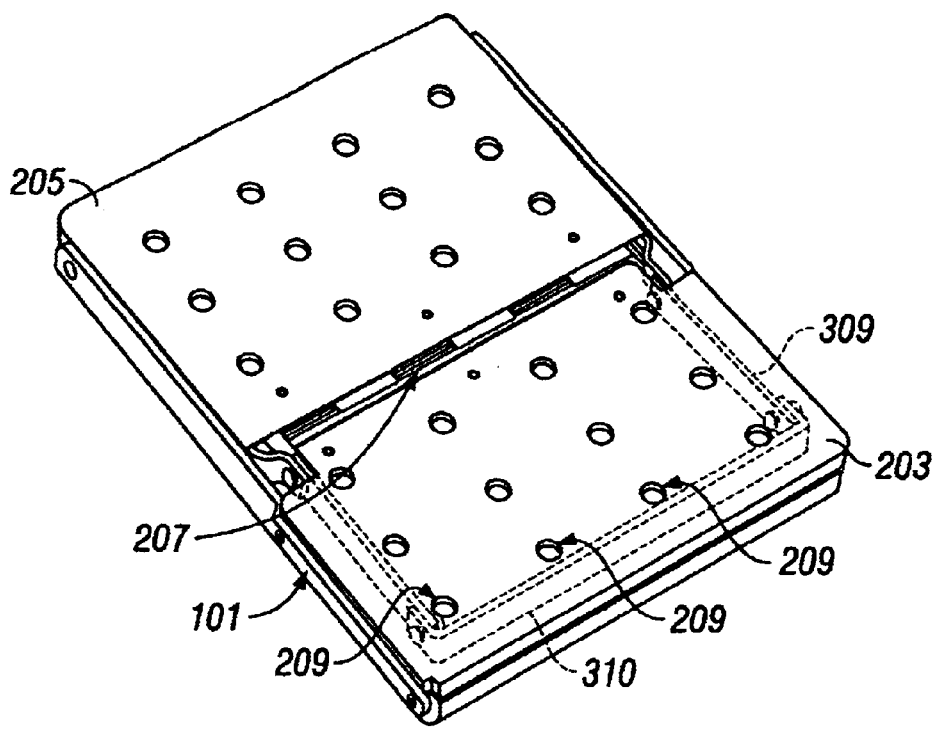
FIG. 2 is an isometric view showing the back cover of the invention, with the door in the closed position.

FIG. 2 shows the back of sterilization case 101, with lower portion 203 and upper portion 205 joined with hinge 207. As with front cover 103, holes 209 in lower portion 203 and upper portion 205 permit instruments inside case 101 to be sterilized without removing them from case 101.

Figure 3:
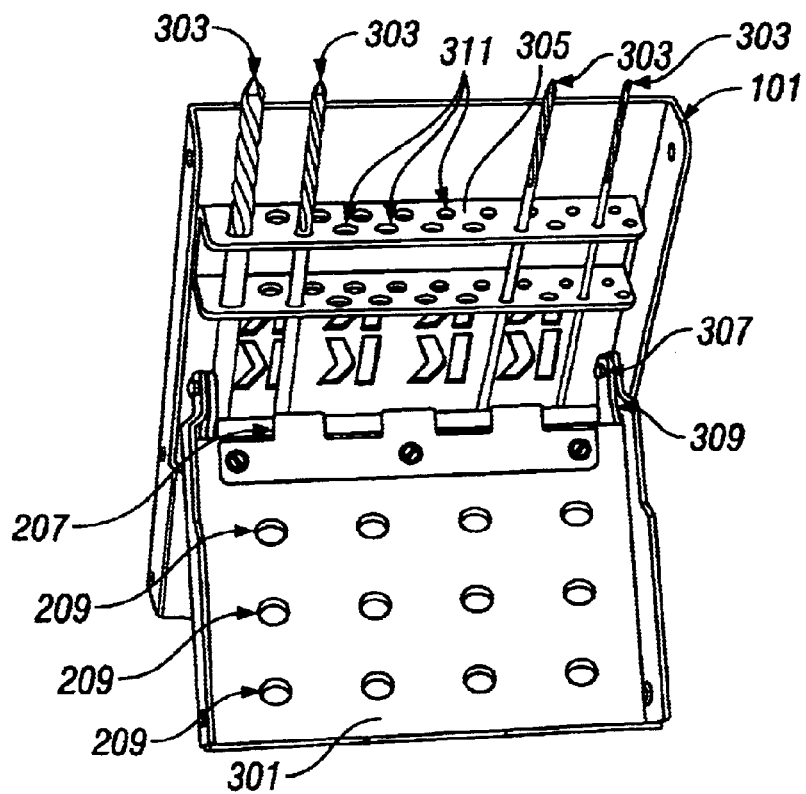
FIG. 3 shows the invention standing upright with the door in the open position.

In FIG. 3, the upper portion of the back cover rotates about hinge 207 to function as door 301 and to allow sterilization case 101 to stand upright. Instruments 303, for example, surgical drill bits, are held in position by guide 305, which has openings 311. Instruments 303 slide through openings 311 in guide 305 until they come to rest against internal tray 310, which is shown in broken lines because it is covered by lower portion 203 and thus hidden from view in FIG. 2. Openings 311 in guide 305 allow storage of a variety of sizes of, e.g., surgical drill bits.

When door 301 is in the open position, as shown in FIG. 3, internal tray is raised by lifting means to elevate instruments 303 above the top level of case 101. In the embodiment shown, the lifting means comprises a linkage arm 309 rotationally attached to an attachment tab 313 of door 301 through a pivot point 307, and similarly attached through a second pivot point to internal tray 310. In this embodiment, each end of internal tray 310 has a linkage arm 309, such that as door 301 rotates about hinge 207 (i.e. as door 301 is opened and closed), the attachment tabs 313 raise or lower, thereby causing linkage arms 309 to raise and lower internal tray 310, thus lifting or lowering instruments 303 which are resting on internal tray 310. Elevation of instruments 303 above the top of sterilization case 101 permits easier removal of instruments 303 (e.g. drill bits) from case 101 during surgery. Although this particular embodiment illustrates a lifting means using linkage arms, other means (for example, wire and pulley, or a spring mechanism) for lifting inner or internal tray 310 may be used without going beyond the scope of the invention.

Figure 4:
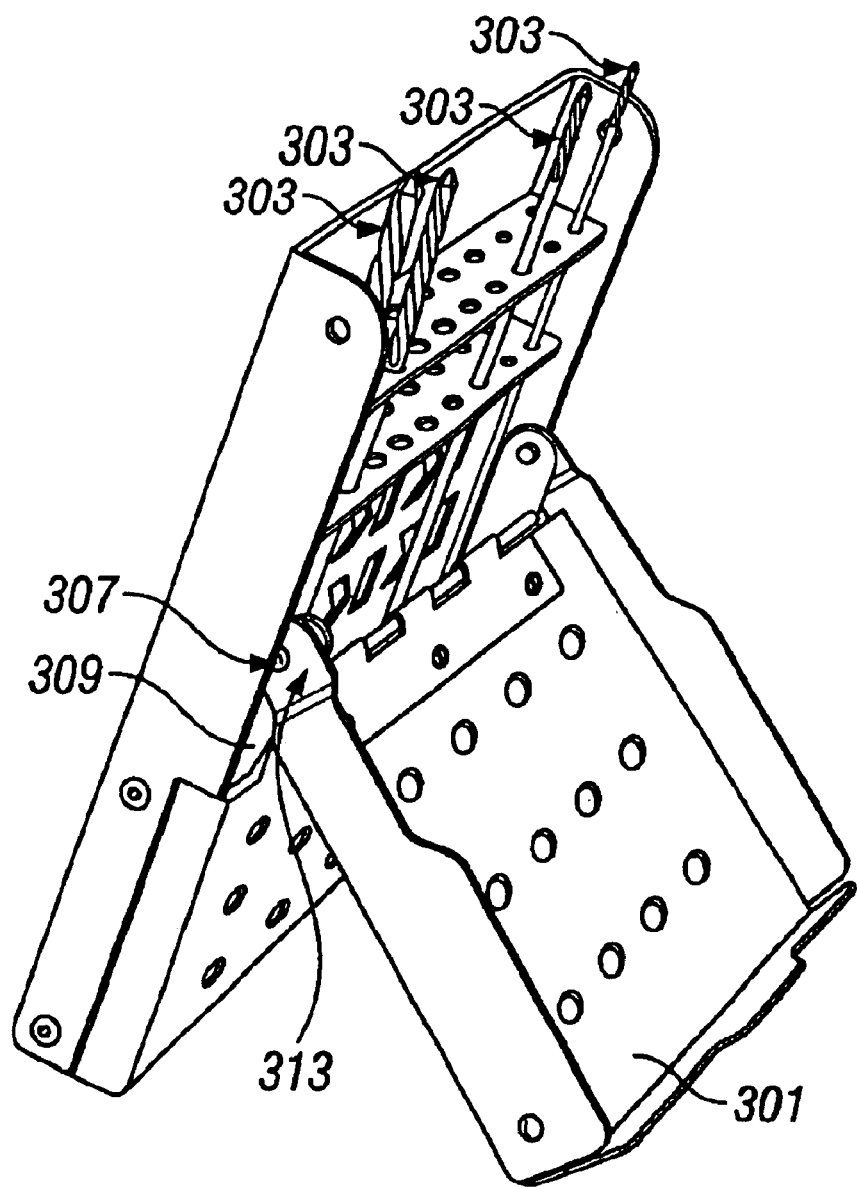
FIG. 4 is an isometric view of the invention standing upright with the door in the open position.

As seen in FIG. 4, sterilization case 101 can rest against open door 301, thus allowing sterilization case 101 to remain standing in an upright position.

Other embodiments or variations are possible without going beyond the scope of the invention as described herein. As described above, embodiments using lifting means other than a linkage arm are possible. The sterilization case may be adapted for surgical instruments other than drill bits. The size, shape, number and location of holes in the covers may be modified so long as the instruments inside the case are sufficiently sterilized. The hinge may be replaced by other mechanisms which allow the door to swing open, for example, a pin joint.

It is apparent from the foregoing that the present invention achieves the specified objects, as well as the other objectives outlined herein. While currently preferred embodiments of the invention have been described in detail, it will be apparent to those skilled in the art that the principles of the invention are readily adaptable to a wide range of other sterilization cases without departing from the scope of the invention.

I claim:

1. A case for surgical instruments, comprising:

a front cover;

a back cover comprising a lower portion and an upper portion pivotally attached to said lower portion;

a guide positioned between said front cover and said back cover and having a plurality of openings;

an internal tray positioned below said guide and between said front cover and said lower portion so that the surgical instruments may slide through said openings in said guide until they come to rest against said internal tray; and a linkage that connects said internal tray to said upper portion whereby rotation of said upper portion relative to said lower portion will raise or lower said internal tray to lift or lower the surgical instruments thereon.

2. The case of claim 1, wherein said upper portion is attached to said lower portion with a hinge.

3. The case of claim 1, said upper portion further comprising an attachment tab, wherein said linkage comprises a linkage arm pivotally attached at one end to said attachment tab of said upper portion and at the other end to said internal tray.

4. The case of claim 1, wherein said upper portion rotates relative to said lower portion to form a support for said case.

5. The case of claim 1, wherein at least one of said front cover and said back cover has openings sufficient to permit sterilization of the surgical instruments inside said case.

* * * * *